(12) United States Patent
Eräluoto

(10) Patent No.: US 9,332,901 B2
(45) Date of Patent: May 10, 2016

(54) OPHTHALMIC APPARATUS AND METHOD FOR MEASURING AN EYE

(75) Inventor: Markku Eräluoto, Espoo (FI)

(73) Assignee: ICARE FINLAND OY, Vantaa (FI)

( * ) Notice: Subject to any disclaimer, the term of this patent is extended or adjusted under 35 U.S.C. 154(b) by 70 days.

(21) Appl. No.: 14/349,545

(22) PCT Filed: Sep. 5, 2012

(86) PCT No.: PCT/FI2012/050857
§ 371 (c)(1),
(2), (4) Date: Apr. 3, 2014

(87) PCT Pub. No.: WO2013/034803
PCT Pub. Date: Mar. 14, 2013

(65) Prior Publication Data
US 2014/0293221 A1    Oct. 2, 2014

(30) Foreign Application Priority Data
Sep. 6, 2011    (FI) ..................... 20115874

(51) Int. Cl.
| | |
|---|---|
| A61B 3/10 | (2006.01) |
| A61B 3/14 | (2006.01) |
| A61B 3/00 | (2006.01) |
| A61B 3/103 | (2006.01) |
| A61B 3/15 | (2006.01) |

(52) U.S. Cl.
CPC .............. *A61B 3/10* (2013.01); *A61B 3/0008* (2013.01); *A61B 3/103* (2013.01); *A61B 3/152* (2013.01)

(58) Field of Classification Search
USPC ............... 351/205, 246, 208, 209, 210, 221
See application file for complete search history.

(56) References Cited

U.S. PATENT DOCUMENTS

| | | |
|---|---|---|
| 5,561,482 A | 10/1996 | Miyake |
| 6,056,404 A | 5/2000 | Kawai |
| 2007/0171363 A1 | 7/2007 | Chen |

FOREIGN PATENT DOCUMENTS

| | | |
|---|---|---|
| EP | 0722690 | 7/1996 |
| EP | 1341119 | 9/2003 |
| EP | 2177151 | 4/2010 |
| WO | 2007084943 | 7/2007 |

*Primary Examiner* — Jack Dinh
(74) *Attorney, Agent, or Firm* — Fasth Law Offices; Rolf Fasth

(57) ABSTRACT

The ophthalmic apparatus is aligned to an eye to be examined. The apparatus is used to examine the eye. It has two or more infrared or near infrared light sources for emitting light beams and a detector sensitive to infrared or near-infrared light with the capability of detecting the light reflected from the examinee's face. It registers the examination result of the eye examined. The ophthalmic apparatus is aligned to an eye to be examined. The light beam of one infrared or near infrared light source is directed to the face. The light beam of another infrared or near infrared light source is directed to pass the examinee. The direction of the light reflected from the examinee's face is detected and the examination result and the examined eye are registered to know whether the examined eye was the right eye or the left eye.

13 Claims, 3 Drawing Sheets

OPHTHALMIC APPARATUS AND METHOD FOR MEASURING AN EYE

PRIOR APPLICATIONS

This is a U.S. national phase patent application that claims priority from PCT/FI2012/050857 filed 5 Sep. 2012, that claims priority from Finnish Patent Application No. 20115874, filed 6 Sep. 2011.

TECHNICAL FIELD

The invention is concerned with an ophthalmic apparatus and a method for measuring an eye.

BACKGROUND OF THE INVENTION

An ophthalmic device or apparatus (also called ophthalmologic device or ophthalmometer) is typically aligned to measure one eye, the right or the left eye, of an examinee and the measuring result is registered by the device. The device can, however, not usually distinguish between the right or the left eye and the registered result, thus, does not involve the information about which eye the result is concerned with.

Since ophthalmologic measurement results, such as those of tonometer measurements, and measurements related to the cornea, are different for the right and the left eye, it is important to know whether the measurement result relates to the right or the left eye of the examinee. For the time being there does not exist any ophthalmic device on the market that would be able to give this information reliably and automatically.

In prior art, some attempts have been made to solve this problem and some methods and means regarding eye related measurements being able to distinguish between the right eye and the left eye have been developed.

U.S. Pat. No. 6,056,404 presents an ophthalmic apparatus with a judging device for judging whether the eye is a right eye or a left eye using results detected by a photo-receiving device based on face boundaries. This document wants to solve the problem that arises when an examiner forgets to input data about whether it was the right eye or the left eye that was examined.

U.S. Pat. No. 5,861,937 presents an ophthalmic apparatus having a calculating unit for judging whether the aligned eye is the right eye or the left eye based on results detected by an optical system. A CCD camera is used for this purpose.

U.S. Pat. No. 5,561,482 presents an eye refractive power measuring apparatus with orientation dependent discrimination between right and left eyes. The apparatus performs a judging whether the eye to be examined is the right eye or the left eye. This solution uses infrared detection for sensing infrared rays emitted by the examinee's face. Infrared light emitted from examinees' faces is, however, quite weak to be detected and is not always possible to be discriminated from the environmental light.

EP patent 0 722 690 B1 relates to an ophthalmologic apparatus with discriminating means for discriminating whether the eye under examination being measured by said measuring device is the left eye or the right eye. Reflecting infrared light is used for that purpose. Even this system, however, is sensitive for errors caused by interfering infrared light from the environment, such as sunshine.

THE OBJECT OF THE INVENTION

The object of the invention is a method and an apparatus which is immune to interference and which has a reliable ability to detect which eye is examined.

SUMMARY OF THE INVENTION

The invention is concerned with an ophthalmic apparatus, which is aligned to an eye to be examined. The apparatus comprises means for examining the eye of an examinee, two or more infrared or near infrared light sources for emitting two or more light beams, a detector sensitive to infrared or near-infrared light with the capability of detecting the light reflected from the examinee's face as a consequence of said emitting, and of detecting the direction from which the light is reflected from the examinee's face and for judging based on the detected direction whether the apparatus is aligned against the examinee's right or left eye for the examination, and means for registering the examination result of the eye and the eye that was examined.

The method of the invention is intended for all kind of ophthalmic examinations including measurements related to the intraocular pressure and the thickness of cornea by using an ophthalmic apparatus, which comprises two or more infrared or near infrared light sources, a detector for detecting infrared or near infrared light, and means for detecting the direction of the reflected infrared or near infrared light. The method comprises aligning the ophthalmic apparatus to an eye to be examined, directing the light beam of one infrared or near infrared light source to the face of the examinee, directing the light beam of another infrared or near infrared light source to pass the examinee, detecting the direction of the infrared or near infrared light reflected from the examinee's face, and registering the examination result and the examined eye in order to know whether the examined eyes was the right eye or the left eye of the examinee.

The preferred embodiments have the characteristics of the sub claims.

The invention is based on infrared light that is sent in two directions and detecting the direction from which the light is reflected from the patient's face. Therefore, the ophthalmic apparatus of the present invention comprises at least two infrared or near-infrared light sources to emit the light and one or more infrared or near infrared detectors to detect which eye the ophthalmic instrument is aligned to.

The distance between the infrared or near-infrared light sources can vary, e.g. depending on the size and type of the ophthalmic apparatus, the size and type of the light sources themselves and depending on practical installation issues. Moreover, an additional influencing factor is the breadth of the emitted light beam, which is different in different light sources and can even be adjusted in some of them. Consequently, also the angle set between the emitted infrared or near-infrared light beams will vary in the implementation of the invention. In a typical tonometer/light source combination in accordance with an embodiment of the invention, the angle can be. e.g. approximately 90°.

The infrared or near-infrared light sources are placed in relation to each other and directed so that when the ophthalmic apparatus is aligned for the eye to be measured, one of the light beams transmitted by one of the light sources is directed towards the nose or approximately the center of the face of the examinee while the other light beam is directed so that the at least the majority of the light beam completely misses the head of the examinee. In some embodiments, the whole beam of the other light source misses the head of the examinee.

The light beam that is directed towards the examinee's face will be reflected back and can be detected by the detector that is sensitive to infrared or near-infrared wavelengths in the same wave length range as the infrared source. The eye to be measured can be figured out based on from which side the reflection is detected.

When the ophthalmic device is e.g. aligned to the patient's right eye, one of the IR light beams that the device sends hits patient's face while the other light beam passes the face. The beam hitting the human face reflects back while the other one does not. The device then detects which light beam reflects back and determines the position of the ophthalmic device in relation to the patient's head.

Infrared (IR) light is electromagnetic radiation with a wavelength between the visible and microwave portions of the electromagnetic spectrum and longer than that of visible light. The wavelength range is from about 1 millimeter down to 750 nm. The range adjacent to the visible spectrum is called "near infrared" and the longer wavelength part is called "far infrared". These wavelengths correspond to a frequency range of approximately 1 to 400 THz. "Visible light" corresponds to a wavelength range of 400-700 nanometers (nm) and a color range of violet through red.

An IR source is any object that emits Infrared radiation. IR-Lasers utilize technologically relevant wavelengths of 850 nm, 1300 nm, 1310 nm, 1550 nm and 1625 nm.

The output from a Light Emitting Diode (LED) can range from red (at a wavelength of approximately 700 nanometers) to blue-violet (about 400 nanometers). Some LEDs emit infrared (IR) energy of 830 nanometers or longer) and these devices are known as infrared-emitting diodes (IREDs) or infrared-light-emitting diodes (IRLEDs). Typical infrared light emitting diodes (IRLEDs) have a peak wavelength of 740 to 950 nm.

IRLEDS convert incoming infrared light to an electric current. The current is sent to a detector device (also called sensor or receiver) that reads the current to determine the strength of incoming light. The infrared transmitter part and receiver part (detector) should be chosen so that their wavelengths match, i.e. work at the same wavelengths.

The invention primarily uses an IR LED as an infrared source to emit the infrared energy but also other IR sources can be used, such as an IR laser of the above kind. .

One possible implementation of such an embodiment of the invention thus has two IR LEDs, one on each side of the ophthalmic device with the IR beams directed at approximately 90 degrees to each other. The device also has an IR detector, which detects the intensity of reflected IR light and its direction.

The IRLEDs are switched on and off one after the other and the detector detects the difference of the intensity of infrared light or near infrared light in these directions at wavelengths of these two beams. One of the intensity values will come in the directions of a beam reflected from the examinee's face. In simple terms, if there is less reflection from the right side, the device is measuring the right eye and vice versa.

The described invention has been designed to solve the above mentioned problems with eye discrimination and makes it possible to automatically detect which eye is being measured. It provides a reliable method for judging whether the ophthalmic apparatus has been aligned to the examinee's right or left eye. It is important to link the measurement result to the correct eye that was measured.

The method and apparatus of the invention is much more reliable than those of prior art and is not affected by disturbances from the environment.

The prior art way of selecting the eye to be measured and recording the measurement result and the eye that was measured manually leads to a possibility of human errors. The reliable automatic eye detection in accordance with the invention will eliminate human errors and link the measurement results to the correct eye.

This is especially useful in e.g. such tonometers, wherein the patients make the measurements by themselves and is generally advantageous for small hand-held ophthalmic instruments that can be easily moved from one eye to the other. Automatic eye detection not only eliminates human errors but also speeds up the measurement or examination process.

Many things besides people and animals emit infrared light, like the earth and the sun. Humans, at normal body temperature, radiate most strongly in the infrared range at a wavelength of about 10 micrometers (microns). Also, many things do not only emit infrared light, they also reflect infrared light, particularly near infrared light.

By using two light sources as in the preferred embodiment of an invention and by switching the light sources on and off alternately, the sensing or detecting of the reflection can be done by one detector. When only one detector is used for detecting the infrared or near-infrared light, the baseline caused by background infrared or near-infrared radiation is the same for both sides of reflection and the background can easily be eliminated.

Alternatively, each side can have its own infrared or near-infrared light source and detector. A further alternative in this embodiment is that is that one light source and detector can in the invention also be combined into one module.

Daylight is a very unpredictable source of infrared with the actinic values altered by both weather and atmospheric haze. Therefore the interference cause by it is a problem at IR detection. Also different other sources give different IR values when detected.

Prior art devices using IR detection to detect reflected IR light from one single source is therefore not very reliable. Such a system is sensitive for errors caused by objects in the vicinity, like hot elements, daylight and the sun.

By using two sources, infrared, or near infrared light, can be sent in two different directions. When these beams are sent alternately within a short time range, the change in the state of radiation from the different directions is identified by the detector. The detector can then also identify from which direction there is more reflection and in this way conclude which eye the ophthalmic apparatus is aligned to.

The invention thus provides a method and an apparatus which both is immune to interference and which has a reliable ability to detect which eye is examined.

The accompanying drawings, together with the following description, serve to explain the principles and advantages of some preferred embodiments of the invention.

DETAILED DESCRIPTION OF PREFERRED EMBODIMENTS

Figure 1:
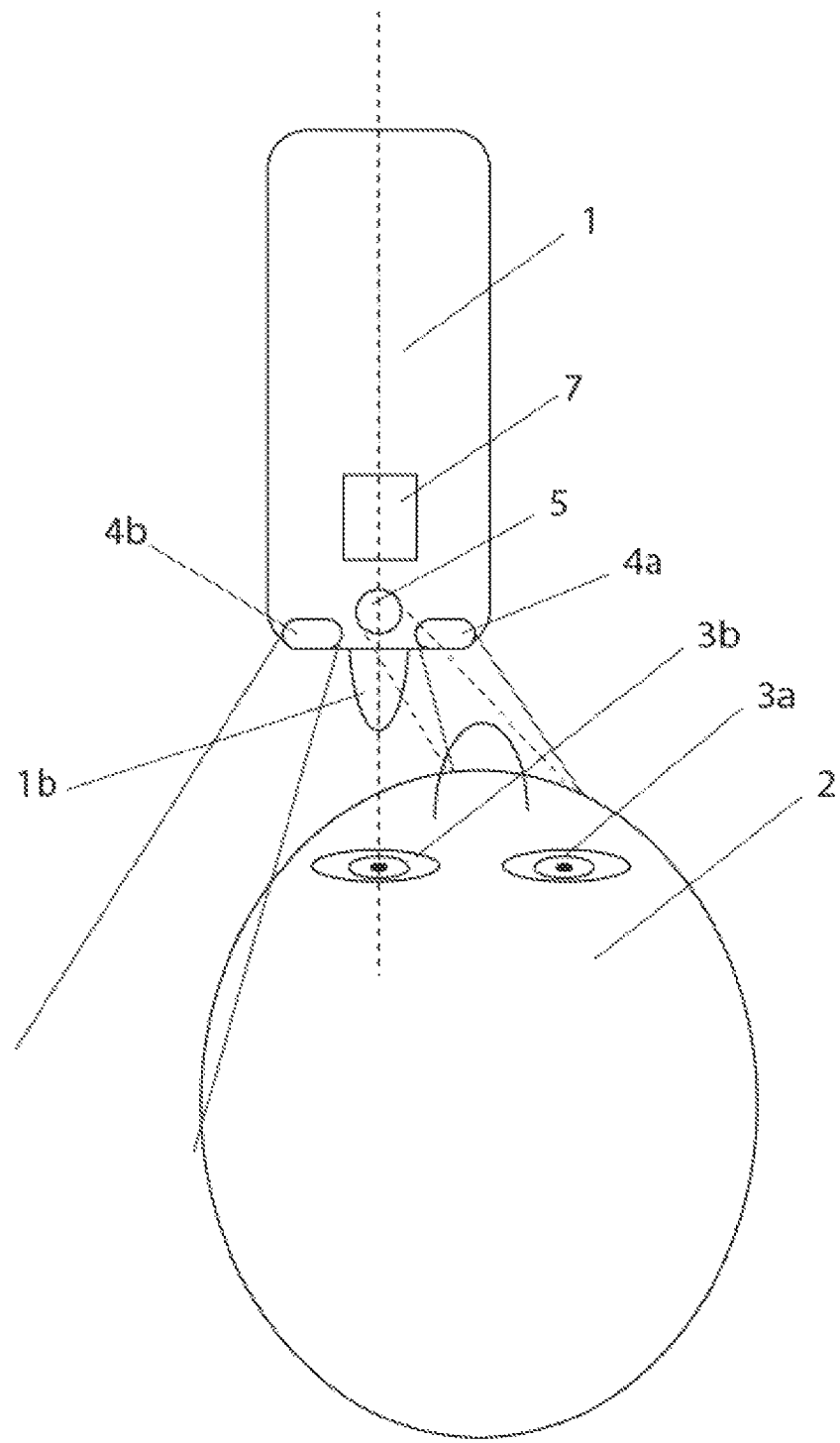
FIG. 1 is an illustration of the ophthalmic apparatus aligned to measure the left eye.

FIG. 1 is an illustration of an ophthalmic apparatus 1 of the invention, when it is aligned to measure the left eye 3b of an examinee by the examining means 1b of the apparatus.

The apparatus of FIG. 1 has two infrared light sources 4a, 4b of which one 4a is in FIG. 1 directed to the center of the examinee's face, and the other infrared light source 4b is directed so that the light beam completely passes outside the head 2 of the examinee. The direction of the light beams is indicated with lines in the figure. The light beams of these sources 4a, 4b can e.g. be 90° in relation to each other. Other angles are possible and the optimal angle depends e.g. on the size of the ophthalmic instrument and the distance between the two light infrared sources. There are also means 7 for registering the examination result of the eye and the eye that was examined.

The detector 5 detects the light that reflects from the examinee's face, which is indicated with dashed lines in FIG. 1.

Figure 2:
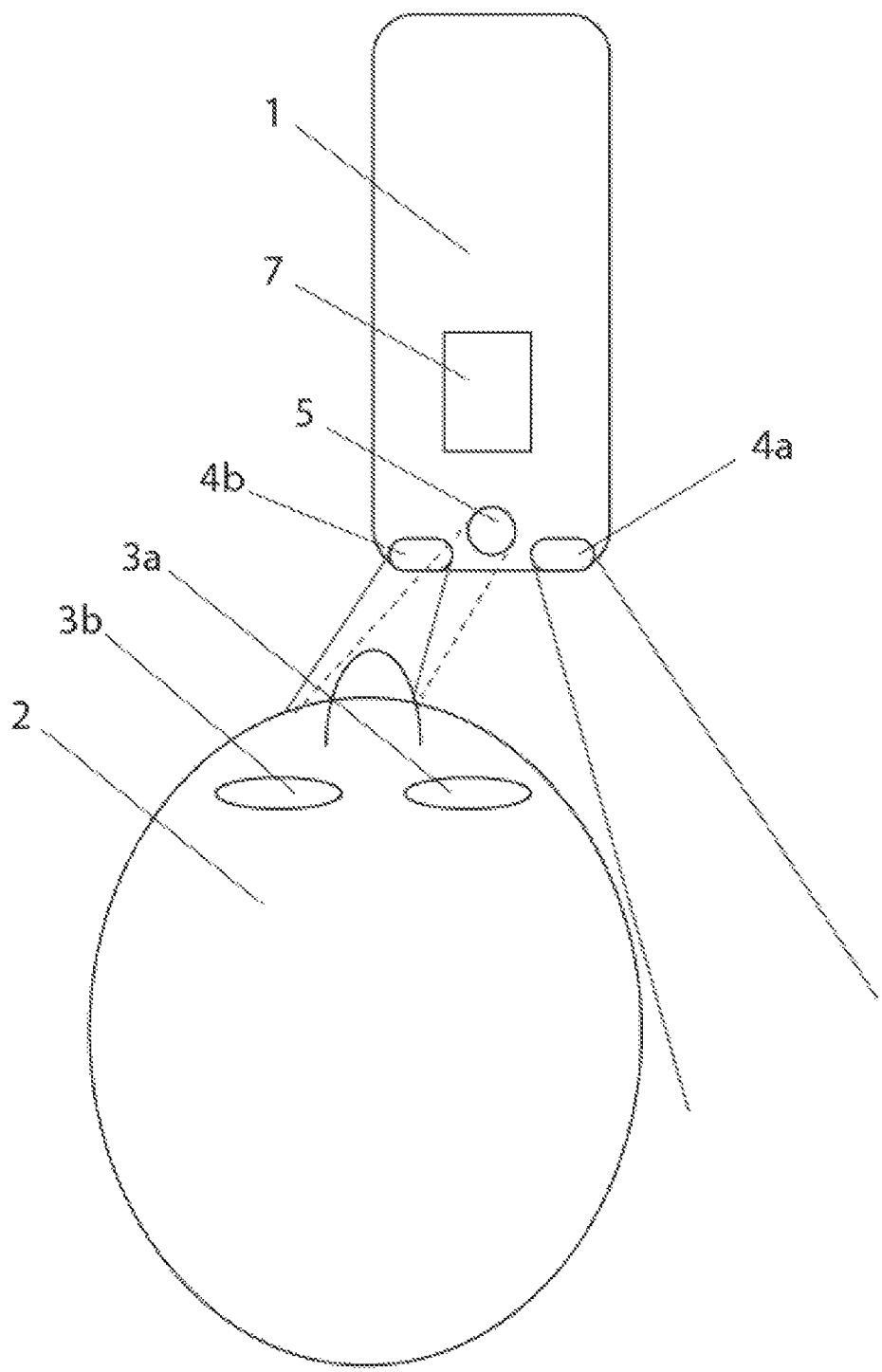
FIG. 2 is an illustration of the ophthalmic apparatus aligned to measure the right eye.

FIG. 2 is an illustration of an ophthalmic apparatus 1 of the invention, when it is aligned to measure the right eye 3a of an examinee. It is the same apparatus as in FIG. 1 just aligned differently.

In FIG. 2 infrared light source 4b is directed to the center of the examinee's face and the other infrared light source 4a is directed so that the light beam completely passes outside the head 2 of the examinee. The direction of the light beams emitted is indicated with lines in FIG. 2.

The detector 5 detects the light that reflects from the examinee's face, which is indicated with dashed lines in FIG. 2.

By switching the light sources on and off alternately, the detection of the reflection can be made by one detector 5 in the embodiment of FIGS. 1 and 2. There is an advantage in using only one detector 5 for the measurements as is done in the embodiments of FIGS. 1 and 2 since the baseline caused by background infrared is near infrared light is the same for both sides of reflection and the background can be easily eliminated.

Figure 3:
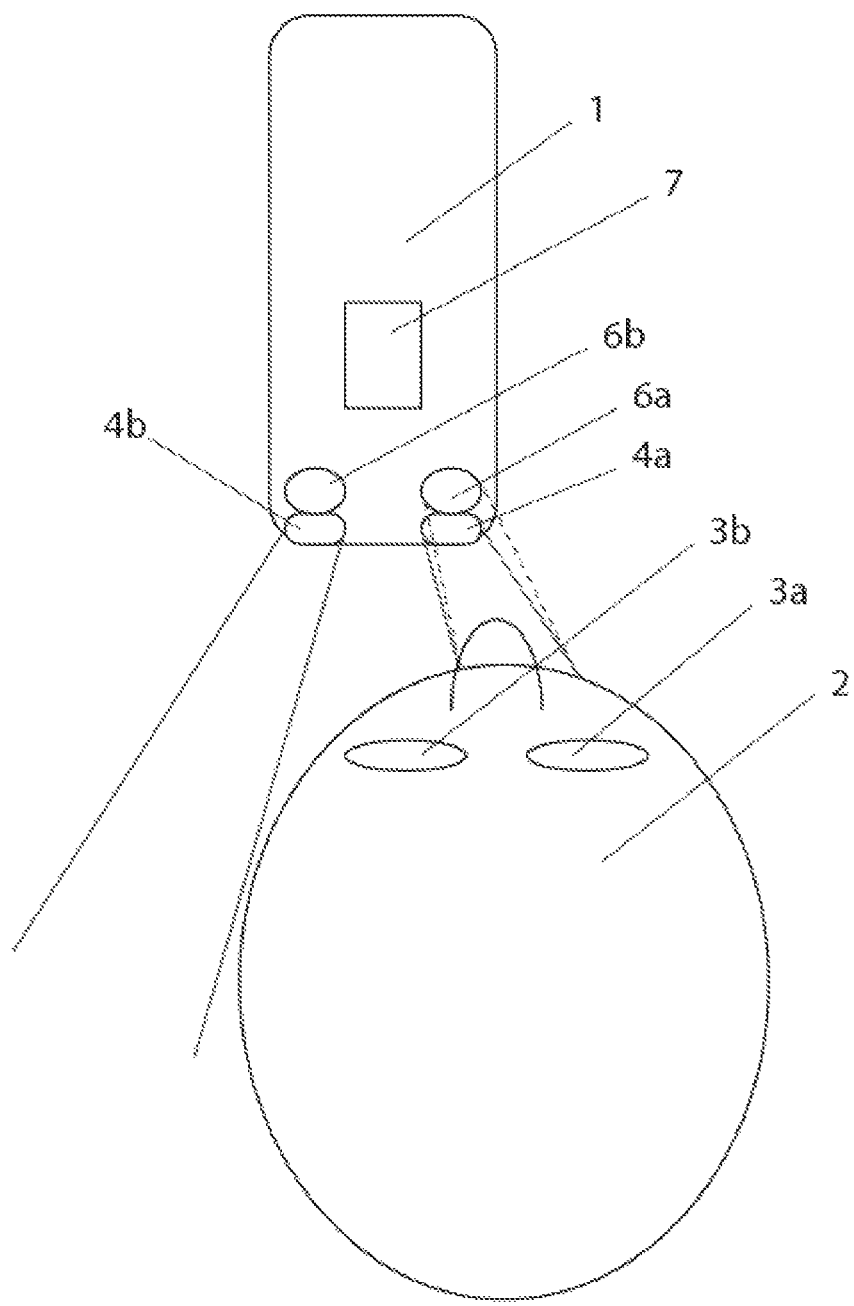
FIG. 3 is an illustration of the ophthalmic apparatus aligned to measure the left eye with the apparatus having alternative sensor arrangement.

FIG. 3 is an illustration of another embodiment of an ophthalmic apparatus 1 of the invention than that of FIGS. 1 and 2. In FIG. 3 the apparatus 1 is aligned to measure the left eye 3b of an examinee.

The apparatus of FIG. 3 has two infrared light sources 4a, 4b of which one 4a is directed to the center of the examinee's face and the other infrared light source 4b is directed so that the light beam completely passes outside the head 2 of the examinee. The direction of the light beams is indicated with lines.

The detector 6a detects the light that reflects from the examinee's face.

There is an other detector 6b that detects the light that reflects from the examinee's face when the light sources are directed vice versa, i.e. when in the measurement, light source 4b is directed to the center of the examinee's face and the other infrared light source 4a so that the light beam completely passes outside the head 2 of the examinee.

A possible sequence for determining which eye the ophthalmic instrument is aligned to is described in the following.

The measured eye is either detected immediately before or after the measurement. The measured eye or the eye to be measured can be detected by the described infrared or near-infrared system.

One of the infrared sources, for example 4a, is first switched on while the other infrared source 4b is switched off. The reflected light intensity and the direction of the reflected light beam are detected using the infrared detector 5 and the results are recorded in the processing unit 7.

Then the second infrared source 4b is switched on and the first infrared source 4a is switched off. The direction of the reflected infrared light beam and its intensity are again detected 5 and recorded by the processing unit 7.

When the ophthalmic instrument 1 (ophthalmic apparatus) is aligned to one of the eyes of the examinee, the reflected infrared intensity is higher from the side where the infrared beam is directed towards the center of the face of the examinee. The difference in the intensity of infrared or near infrared light in the two directions is then calculated and based on this difference, the measured eye can be detected.

A threshold value for the difference can be set for controlling of the accuracy of the detection. The threshold can be used to decide whether the difference between the two recorded reflections is large enough to obtain a reliable result. If the difference is not large enough, it can be assumed that the instrument is incorrectly aligned or not aligned to a patient at all, which could lead to an erroneous result. The misalignment can be indicated to the patient as an error indication.

This technology allows for a very fast detection of the measured eye. The detection can be made in a fraction of a second and does not slow down the measurement sequence.

I claim:

1. An ophthalmic apparatus being aligned to an eye to be examined, the apparatus comprising:
    means for examining the eye of an examinee,
    a first infrared or near infrared light source adapted to emit light beams in a first direction,
    a second infrared or near infrared light source adapted to emit light beams in a second direction, the first direction being different from the second direction,
    the light sources being adapted to be switched on and off alternately,
    a detector sensitive to infrared or near-infrared light with the capability of detecting the light reflected from the examinee's face as a consequence of said emitting, and of detecting the direction from which the light is reflected from the examinee's face,
    means for judging based on the detected direction, based on a difference in intensity of the light in the directions of the first light beam and the second light beam, whether the apparatus is aligned against the examinee's right or left eve for the examination, and for registering the examination result of the eye and the eye that was examined, and
    said infrared or near infrared light sources being associated with different eyes and directed to emit light in different directions in such a way that one of the said light sources is directed for emitting a light beam in the direction of the examinee's face, and the other of said light sources is directed for emitting a light beam so that at least a majority of the light beam misses the examinee's face.

2. An ophthalmic apparatus according to claim 1, wherein said infrared or near-infrared light sources are directed so that when the said apparatus is aligned to the eye to be examined, one of the said light sources emits a light beam that is directed towards the nose or essentially the center of the face of the examinee and the other said light source emits a light beam that is directed so that the majority of the light beam passes the head of the examinee.

3. An ophthalmic apparatus according to claim 1, wherein said infrared sources are Infrared Light Emitting Diodes (IR LEDs).

4. An ophthalmic apparatus according to claim 1, wherein said infrared sources are positioned on each side of the ophthalmic apparatus and positioned so that they can emit infrared or near infrared beams in directions giving different reflections.

5. An ophthalmic apparatus according to claim 1, wherein said detector can detect infrared or near infrared light within the same wavelength range as the infrared or near infrared sources.

6. An ophthalmic apparatus according to claim 1, wherein the infrared or near-infrared light sources are directed so that when the apparatus is aligned to the eye to be examined, one of the light sources emits a light beam that is directed towards the nose or essentially the center of the face of the examinee and the other light source emits a light beam that is directed so that the light beam completely misses the head of the examinee.

7. A method for ophthalmic measurements, by using an ophthalmic apparatus comprising two or more infrared or near infrared light sources, a detector for detecting infrared or near infrared light, the method comprising:

aligning the ophthalmic apparatus to an eye to be examined, directing a first light beam of a first infrared or near infrared light source in a first direction of a face of an examinee, directing at least the majority of a second light beam of a second infrared or near infrared light source in a second direction to pass a head of the examinee, the first direction being different from the second direction, alternately, switching on and off the infrared or near-infrared light sources, detecting a direction of the infrared or near infrared light from the first light beam or the second light beam reflected from the examinee's face by detecting a difference in an intensity of an infrared or near infrared light in a direction of a reflected beam and in a direction of a beam that was emitted in another direction that passed the head of the examinee, judging based on the direction whether the apparatus is aligned against the examinee's right eye or left eye for examination, and registering the examination result and the examined eye.

8. The method of claim 7, wherein said infrared or near infrared light beams are directed in different directions to give different reflections.

9. The method of claim 8 wherein the method further comprises the steps of detecting the infrared light or near infrared light of the environment without the emission from the infrared sources and registering the change in the state of radiation by comparing it to the reflected light identified by the detector at emitting with the infrared or near infrared sources.

10. The method of claim 8 wherein the detector identifies in which direction there is more reflection and uses this information as a basis in order to conclude which eye the ophthalmic apparatus is directed on.

11. The method of claim 8, wherein a threshold value is set for the detected infrared or near infrared light, which has to be exceeded for the result to be used.

12. The method of claim 7 wherein the infrared or near infrared light beams of the two sources are sent alternately within a short time range.

13. A method for ophthalmic measurements, by using an ophthalmic apparatus comprising two or more infrared or near infrared light sources, a detector for detecting infrared or near infrared light, the method comprising:

aligning the ophthalmic apparatus to an eye to be examined, directing a first light beam of a first infrared or near infrared light source in a first direction of a face of an examinee, directing a second light beam of a second infrared or near infrared light source in a second direction so that at least a majority of the second light beam passes a head of the examinee, the first direction being different from the second direction, detecting whether the first light beam or the second light beam is reflected from the examinee's face, judging based on which light beam is reflected whether the apparatus is aligned against the examinee's right eye or left eye for examination, and registering the examination result and the examined eye.

* * * * *